United States Patent
Shu et al.

(10) Patent No.: US 8,852,225 B2
(45) Date of Patent: Oct. 7, 2014

(54) EMBOLI GUARDING DEVICE

(75) Inventors: Mark C. S. Shu, Rancho Santa Margarita, CA (US); Angela Shu, legal representative, Rancho Santa Margarita, CA (US); Charles Paul Tabor, Medicine Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 865 days.

(21) Appl. No.: 12/567,243

(22) Filed: Sep. 25, 2009

(65) Prior Publication Data
US 2010/0076482 A1    Mar. 25, 2010

Related U.S. Application Data

(60) Provisional application No. 61/099,935, filed on Sep. 25, 2008.

(51) Int. Cl.
| | | |
|---|---|---|
| *A61M 29/00* | (2006.01) | |
| *A61F 2/01* | (2006.01) | |
| *A61F 2/86* | (2013.01) | |
| *A61F 2/856* | (2013.01) | |

(52) U.S. Cl.
CPC ............. *A61F 2/01* (2013.01); *A61F 2230/008* (2013.01); *A61F 2/86* (2013.01); *A61F 2230/0069* (2013.01); *A61F 2230/0006* (2013.01); *A61F 2/856* (2013.01); *A61F 2002/018* (2013.01)
USPC ......................................... 606/200; 623/1.15

(58) Field of Classification Search
CPC ............. A61F 2/00; A61F 2/01; A61F 2/013; A61F 2/856; A61F 2/86; A61F 2/90; A61F 2/91

USPC .......................................... 606/200; 623/1.15
See application file for complete search history.

(56) References Cited

U.S. PATENT DOCUMENTS

| | | | | |
|---|---|---|---|---|
| 4,629,459 | A | * | 12/1986 | Ionescu et al. ............... 623/2.15 |
| 6,258,120 | B1 | * | 7/2001 | McKenzie et al. ........... 623/1.36 |
| 6,336,934 | B1 | * | 1/2002 | Gilson et al. .................. 606/200 |
| 6,348,063 | B1 | * | 2/2002 | Yassour et al. ................ 606/200 |
| 6,499,487 | B1 | * | 12/2002 | McKenzie et al. ............. 128/898 |
| 6,547,760 | B1 | * | 4/2003 | Samson et al. ........... 604/103.01 |
| 6,692,513 | B2 | | 2/2004 | Streeter et al. |
| 6,769,434 | B2 | | 8/2004 | Liddicoat et al. |
| 7,438,721 | B2 | * | 10/2008 | Doig et al. .................... 623/1.15 |
| 7,470,284 | B2 | | 12/2008 | Lambrecht et al. |
| 2002/0169474 | A1 | | 11/2002 | Kusleika et al. |
| 2003/0100940 | A1 | * | 5/2003 | Yodfat ........................ 623/1.15 |
| 2004/0088062 | A1 | | 5/2004 | Minamimoto |
| 2004/0093014 | A1 | | 5/2004 | Ho et al. |

(Continued)

FOREIGN PATENT DOCUMENTS

| | | |
|---|---|---|
| WO | 2008/033845 | 3/2008 |
| WO | 2008/033895 | 3/2008 |
| WO | 2010/081025 A1 | 7/2010 |

*Primary Examiner* — Katherine Dowe
*Assistant Examiner* — Martin T Ton

(57) ABSTRACT

A device including a stent structure or frame to which a sheet is attached for use in minimizing or preventing emboli, particles, and/or air bubbles from migrating into certain areas of the anatomy. The device can be placed in the blood stream in an area of the heart, such as the aortic arch, to direct particles toward the descending aorta rather than toward the brain. The sheet of the device can be a thin film material, which may include multiple fenestrations that are smaller in size than the particles that are to be filtered.

16 Claims, 4 Drawing Sheets

(56) References Cited

U.S. PATENT DOCUMENTS

| | | | |
|---|---|---|---|
| 2004/0215167 A1* | 10/2004 | Belson | 604/526 |
| 2005/0010285 A1 | 1/2005 | Lambrecht et al. | |
| 2005/0015112 A1 | 1/2005 | Cohn et al. | |
| 2005/0261759 A1 | 11/2005 | Lambrecht et al. | |
| 2006/0161241 A1* | 7/2006 | Barbut et al. | 623/1.15 |
| 2006/0241678 A1 | 10/2006 | Johnson et al. | |
| 2006/0287670 A1 | 12/2006 | Pal | |
| 2008/0065145 A1 | 3/2008 | Carpenter | |

\* cited by examiner

US 8,852,225 B2

EMBOLI GUARDING DEVICE

CROSS-REFERENCE TO RELATED APPLICATION

This application claims the benefit under 35 U.S.C. §119(e) of U.S. Provisional Patent Application No. 61/099,935, filed Sep. 25, 2008, which is incorporated herein by reference in its entirety.

TECHNICAL FIELD

The present invention relates to devices and delivery systems that can be used in heart structures for the prevention of strokes. More particularly, the invention relates to devices, methods, and delivery systems for preventing undesirable movement of emboli within a heart structure.

BACKGROUND

Large or small embolic particles or emboli can be formed for a number of reasons in the left atrium or in other parts of the heart, such as can occur when surgically implanting prosthetic devices into a patient's anatomy. When such particles or emboli are present in the atrium, they have the potential to migrate toward the brain at the arch of the aorta, and can thereby impose potential risk of stroke. Thus, there is a need to provide devices and delivery systems that can filter or guard against undesired emboli migration within the heart or other bodily structures of a patient.

SUMMARY

This invention provides devices, methods, and delivery systems that can be used to prevent or minimize the possibilities of a person having a stroke due to migration of emboli, particles, and/or air bubbles into undesired areas of the anatomy. The device accomplishes this by directing particle flow in a bloodstream in such a way that any particles within that bloodstream are directed along a path where such particles will not be detrimental to the health of the patient. One embodiment of the invention includes a device that consists of a stent structure or frame to which a Nitinol thin film or pericardial sheet is attached in at least one area. The Nitinol thin film or pericardial sheet can be affixed diametrically across the stent diameter at a distal segment of the stent, in one embodiment, although it is also possible that the device includes different placement of the film or sheet and/or that the device includes multiple areas having a film or sheet. Fenestrations with various desired dimensions can be created on the thin film to allow blood to flow through it. If necessary, side channels between the film or pericardial sheet and the wall of the structure in which the device is located can also be created.

The stent structure or frame of the device can be used to anchor the device into the arch of an aorta, for example. In this way, when emboli flow through the aortic arch, the thin film or pericardial sheet of the device can block the flow of emboli toward the carotid arteries or other cerebrovascular structures, and instead allow their movement with the blood flow to carry emboli toward the descending aorta. Thus, the use of the device of the invention can help to prevent brain stroke for a patient.

The devices of the invention can be percutaneously delivered using a transcatheter delivery system to a location in a patient, such as aortic arch. These devices can also be retrieved using a transcatheter retrieval device if needed. The emboli guarding devices can be used as a permanent implantable device at the aortic arch to prevent brain strokes, or as a temporary device to prevent brain stroke during any prosthetic device implantation or a transcatheter valve deployment, for example.

In another aspect of the invention, a guide catheter is provided, which includes an embolic filter positioned between its proximal and distal ends. The filter can be positioned in a desired location in a patient to provide particle filtration. In another aspect of the invention, an embolic guard centering delivery system is provided, which includes an expandable mesh portion that can provide both embolic protection and a centering function. In yet another aspect of the invention, a guide catheter with an expandable mesh portion is provided. The mesh of the guide catheter can provide both embolic protection and a centering function to a device through which other devices, such as delivery systems, can be advanced to a desired anatomical location.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
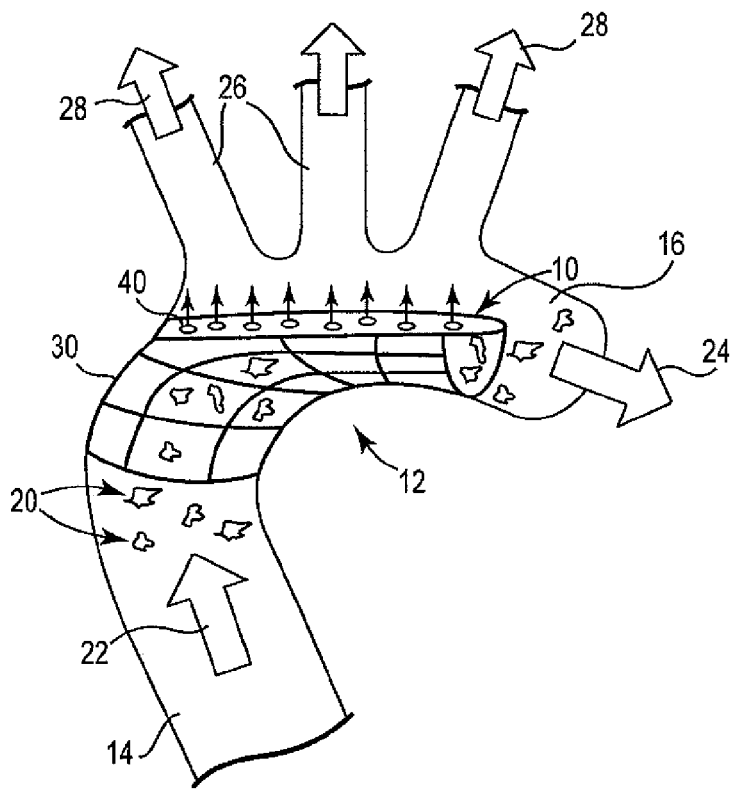
FIG. 1 is a schematic cross-sectional front view of an emboli guarding device of the invention positioned within a heart structure.

Referring now to the Figures, wherein the components are labeled with like numerals throughout the several Figures, and initially to FIG. 1, one embodiment of an emboli guarding device 10 is illustrated in an exemplary position within the anatomy of a patient. In particular, the device 10 is shown here as being positioned within an aortic arch 12, between the ascending aorta 14 and the descending aorta 16. Multiple particles or emboli 20 are illustrated as being randomly dispersed throughout the stream of blood. These particles 20 tend to flow in the main flow stream, which is indicated with arrow 22 in the area of the ascending aorta 14 and with the arrow 24, which is on the opposite side of the device 10 and in the area of the descending aorta 16. The emboli guarding device 10 alters the flow direction and guides emboli 20 and/or air bubbles carried by the flow stream toward the descending aorta 16, rather than toward the head vessels 26 (i.e., the brachiocephalic trunk, the left common carotid artery, and the left subclavian artery) and in the direction of arrows 28. Such an alternative flow of emboli 20 can thereby help to prevent potential brain strokes and/or minimize the chances of migraines and other health issues. It is noted that the emboli and/or air bubbles within the blood stream can be created in a variety of manners, such as from atrial fibrillation (AF), from prosthetic heart valves, from left ventricular assist devices (LVAD's), and/or from any other sources of emboli.

Figure 2:
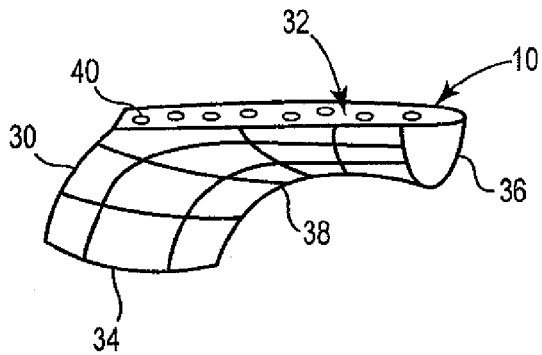
FIG. 2 is a front view of an embodiment of an emboli guarding device, including a film or sheet including small fenestrations.
Figure 3:
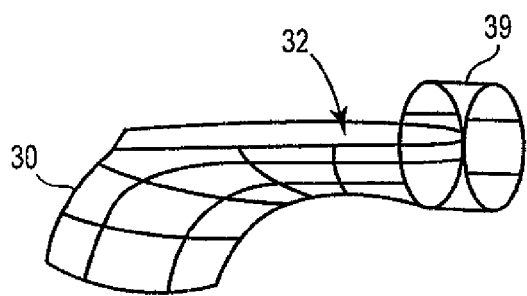
FIG. 3 is a front view of another embodiment of an emboli guarding device, including another embodiment of a film or sheet including small fenestrations.

Referring also to FIGS. 2 and 3, one embodiment of an emboli guarding device 10 consists generally of a frame 30 and a sheet of material 32 that is positioned generally across its upper portion. The frame 30 may be made of a material that is capable of being compressed and expanded, which can be advantageous for percutaneous delivery of the frame 30 to its desired location within the heart. In one example, the frame 30 is made of a material that is expandable via the application of an outwardly directed internal force, such as the force that can be applied with an expandable balloon positioned within the internal opening or area of the frame 30. In another example, the frame 30 is made from a self-expanding material, such as a Nitinol mesh material. In this way, the device 10 can be compressed to a size that allows it to be delivered percutaneously to the desired location via a delivery system, and then allowed to expand by removing or retracting a compressive sheath, for example.

The materials from which the frames 30 of the invention are generally made include a series of wires arranged into a generally elongated tubular support structure. The structure can include one or more linear portions and/or one or more curved, bent, or otherwise shaped portions, in order to provide an optimal fit within an area of the heart. The support structure of the frame 30 may either be made up of a number of individual struts or wire segments arranged and secured to each other. Alternatively, the frame 30 may instead be formed from a single piece of material (e.g., a tube of material that is machined to provide a desired structure configuration). That is, in one exemplary embodiment, the frame 30 may be laser cut from a single piece of material or may be assembled from a number of different components.

As described above, the frames 30 of the invention can be compressible to a relatively small diameter for percutaneous delivery to the heart of the patient, and then are expandable either via removal of external compressive forces (e.g., self-expanding frames), or through application of an outward radial force (e.g., balloon expandable frames). In a further alternative, some portions of the frame 30 may be self-expanding while other portions of the same frame are expandable through application of an externally applied force. In yet another alternative, the frames of the invention can be self-expandable from a contracted state to an expanded state via the application of heat, energy, and the like.

Methods for insertion of the emboli guarding devices of the invention can include delivery systems that can maintain the frames in their compressed state during their insertion and allow or cause all or specific features of the frames to expand once they are in their desired location. In addition, delivery methods of the invention can further include features that allow the emboli guarding devices to be retrieved for removal or relocation thereof after they have been deployed from their delivery systems. The methods of the invention may include implantation of the devices using either an antegrade or retrograde approach. Further, in certain approaches for delivering the devices 10 of the invention, the devices can be rotatable in vivo to allow the stent structure to be positioned in a desired orientation. In one embodiment, a portion of the device 10, such as the frame 30, can include a radiopaque, echogenic, or MRI visible material to facilitate visual confirmation of proper placement of the frame 30 relative to the anatomy of the patient. Alternatively, other known surgical visual aids can be incorporated into the frame 30, if desired.

In another alternative embodiment, the device 10 can be delivered to the patient's anatomy via a minimally invasive surgical incision (i.e., non-percutaneously). In yet another alternative embodiment, the device 10 can be delivered via open heart/chest surgery.

The frame 30 of the device 10 is generally tubular in shape, defining an internal area that extends from a first end 34 to a second end 36. The internal area is essentially surrounded by the frame 30 and the sheet of material 32. The frame 30 can be configured to have an arc portion 38 that is designed and/or chosen to generally match the anatomy of the aortic arch of the patient in order to keep it from being dislodged once it is in place. Thus, the frames can be provided in various lengths and/or shapes to accommodate the different sizes and/or shapes of different patient anatomies. While the exemplary frames 30 of FIGS. 2 and 3 are similarly configured, the frame 30 of FIG. 3 includes an extension portion 39 at its second end 36 that can provide additional anchoring capability relative to the vessel in which it is positioned. A frame may include one or more extensions of this type and/or other features that provide such an anchoring capability.

The material or materials from which the sheet of material 32 is made can vary widely, but generally include a relatively thin piece of material, such as pericardium or a polymer sheet, for example. In another alternative, a thin piece of Nitinol material can be used. With any of these materials, a number of fenestrations or openings 40 can be provided across the area of the sheet 32, as illustrated in FIGS. 1 and 2. These fenestrations 40 can be sized to be smaller than approximately 60µ, although the fenestrations can be any size that allows some blood flow through the surface of the sheet 32 while blocking the movement of the emboli 20 through the sheet 32. Thus, the size of the fenestrations 40 can be selected to effectively filter a size of emboli or particles 20 that would be detrimental to the health of a patient if they were to move through the sheet 32 in the direction of the arrows 28.

One method of delivering the device to a desired location in a patient is via percutaneous device insertion. In general terms for this exemplary delivery system, a transcatheter assembly can be provided, including a delivery catheter, a balloon catheter, and a guide wire. The delivery catheter can be of a type known in the art that defines a lumen within which the balloon catheter is received. The balloon catheter, in turn, can define a lumen within which the guide wire is slidably disposed. Further, the balloon catheter can include a balloon that is fluidly connected to an inflation source. It is noted that if the frame being implanted is a self-expanding type of frame, the balloon would not be needed and a sheath or other restraining means would instead be used, for maintaining the frame in its compressed state until deployment of the device. In any case, the transcatheter assembly is appropriately sized for a desired percutaneous approach. For example, the transcatheter assembly can be sized for delivery to the heart via an opening at a carotid artery, a jugular vein, a sub-clavian vein, femoral artery or vein, or the like. Essentially, any percutaneous intercostals penetration can be made to facilitate use of the transcatheter assembly.

In the case of a balloon-expandable frame, once the frame 30 is properly positioned relative to the anatomy of the patient, the balloon catheter is operated to inflate the balloon, thereby expanding the frame 30 to the expanded state shown in FIG. 1. Alternatively, if the frame 30 is formed of a shape memory material, the frame can be allowed to self-expand to the expanded state of FIG. 1, such as by removing the external forces applied by a sheath. In either case, the frame 30 is preferably expandable within the internal region of the implantation area of the patient with sufficient outward radial force against the anatomical structure (e.g., the aortic arch area) that it cannot become unintentionally dislodged from this area of the patient.

The techniques described above relative to placement of the device 10 within the heart can be used both to monitor and correct the placement of the device 10 in a longitudinal direction relative to the length, shape, and the like of the anatomical structure in which it is positioned and also to monitor and correct the orientation of the device 10 relative to any other structures that may also be implanted in this area.

It is noted that the emboli guarding devices 10 of the invention may be designed for permanent placement within the patient, or may alternatively be removable after a certain period of time. In one embodiment, the device 10 can be removed percutaneously, such as with the use of a system that can recompress the frame 30 by a sufficient amount to remove it in this minimally invasive manner. In another embodiment, the device 10 may need to be removed in a more invasive manner, such as via more conventional surgical techniques.

Figure 4:
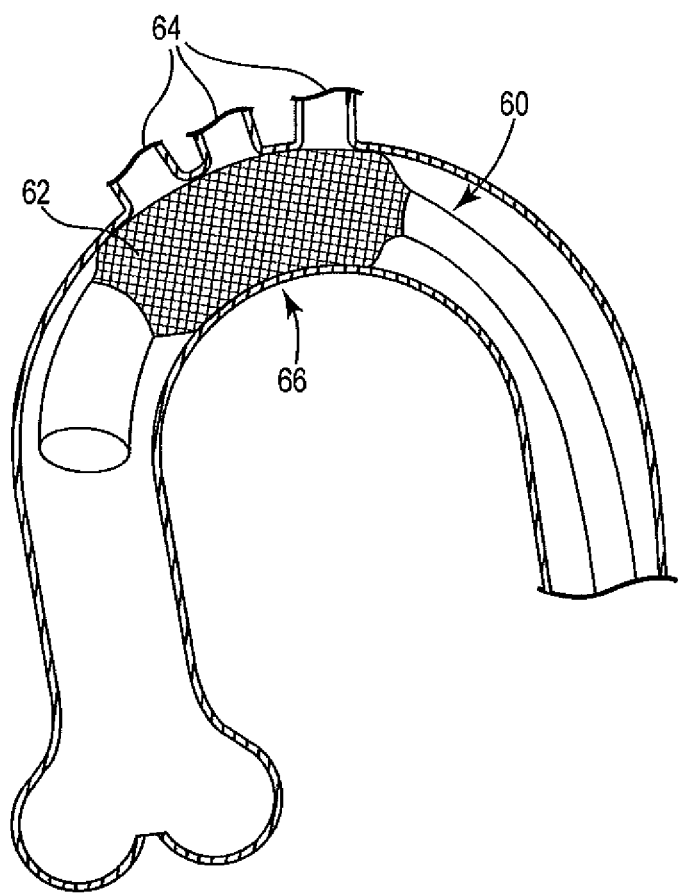
FIG. 4 is a front view of another embodiment of an emboli guarding device of the invention positioned within a schematic heart structure.

FIG. 4 illustrates an alternative embodiment of the invention, which includes an embolic guard guide catheter 60 that is shown as positioned within the aortic arch 66 of a patient. In this embodiment, the guide catheter 60 includes an embolic filter 62 positioned between proximal and distal ends of the catheter 60. The embolic filter 62 can be delivered to the desired location in the patient in order to provide similar filtering features to those described above relative to FIGS. 1-3. In this example, the catheter 60 can localize the embolic filter 62 at the location of the head vessels 64. The length of the filter 62 can be selected to achieve certain performance characteristics, such as being sufficiently long to span across the all of the head vessels 64. The filter 62 may include one or more areas having a thin film, which may or may not include fenestrations, as described above relative to the films that can be used in accordance with the invention.

Figure 6:
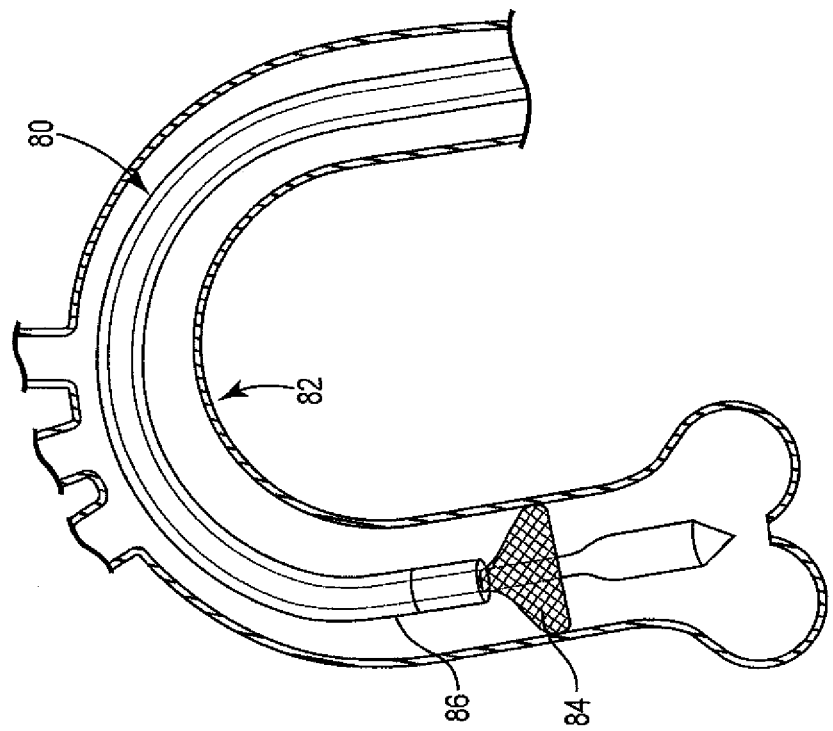
FIG. 6 is another front view of the emboli guarding device of FIG. 5, with the self-expanding mesh structure in an expanded condition within the heart structure.
Figure 5:
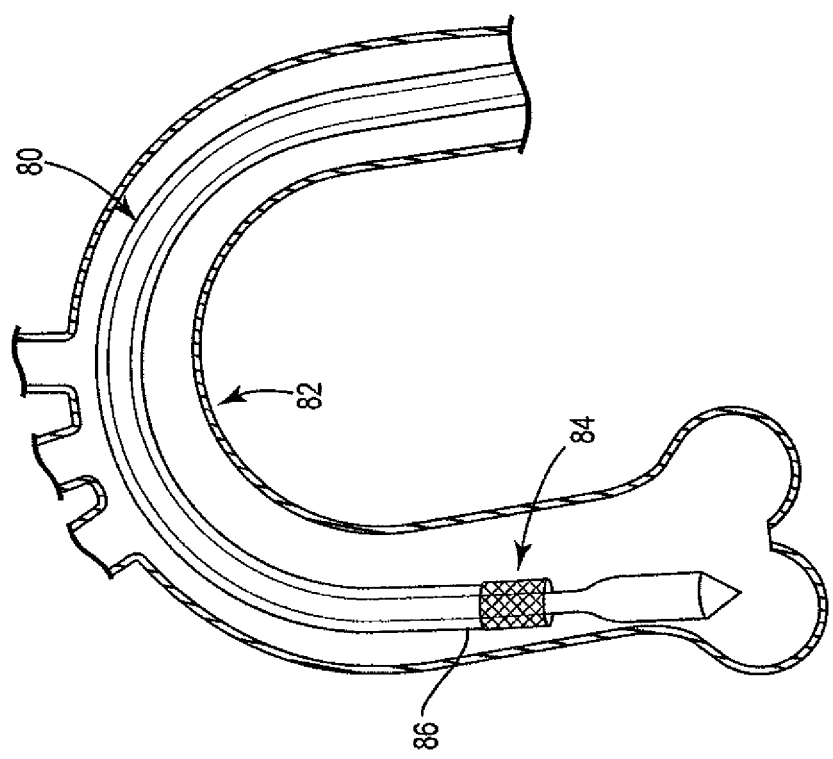
FIG. 5 is a front view of another embodiment of an emboli guarding device on a delivery system within a heart structure, with a self-expanding mesh structure in a collapsed condition.

FIGS. 5 and 6 illustrate another embodiment of the invention, which includes an embolic guard centering delivery system 80 that is shown as positioned within the aortic arch 82 of a patient. In particular, FIG. 5 shows the system 80 with a self-expanding mesh portion 84 in a compressed or collapsed condition relative to a delivery system stability layer 86. Further, FIG. 6 shows the system 80 with the mesh portion 84 in an expanded condition. In order to expand in this way, the stability layer 86 can be pulled proximally to release the mesh portion 84, thereby allowing it to expand to the size and shape of the vessel in which it is positioned. In this way, the mesh portion 84 can provide embolic protection during delivery of a device. That is, the mesh portion 84 is made of a material or materials that allow blood flow, yet that filter out emboli, particles, and/or air bubbles that are undesirably large. Further, the mesh portion 84 may comprise wires and/or film materials that provide the desired level of particle filtering. It is further noted that the expansion of the mesh portion 84 provides a centering function for the delivery system 80 within the ascending aorta. In this way, better coaxial alignment can occur between a transcatheter valve that is being delivered via the delivery system and the annulus during positioning and release thereof, for example.

Figure 8:
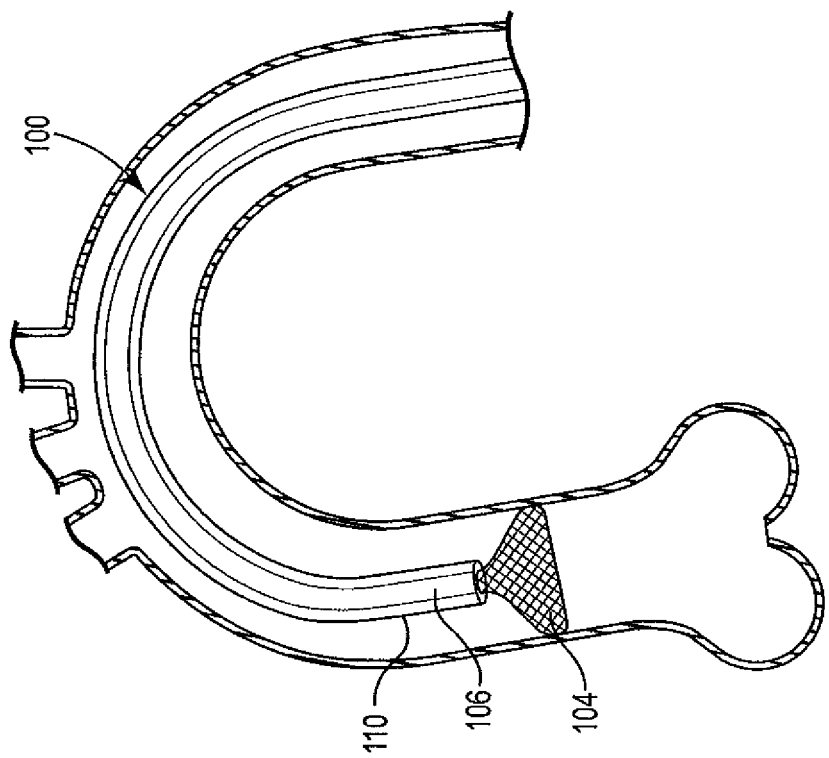
FIG. 8 is another front view of the emboli guarding device of FIG. 7, with the mesh structure in an expanded condition within the heart structure.
Figure 7:
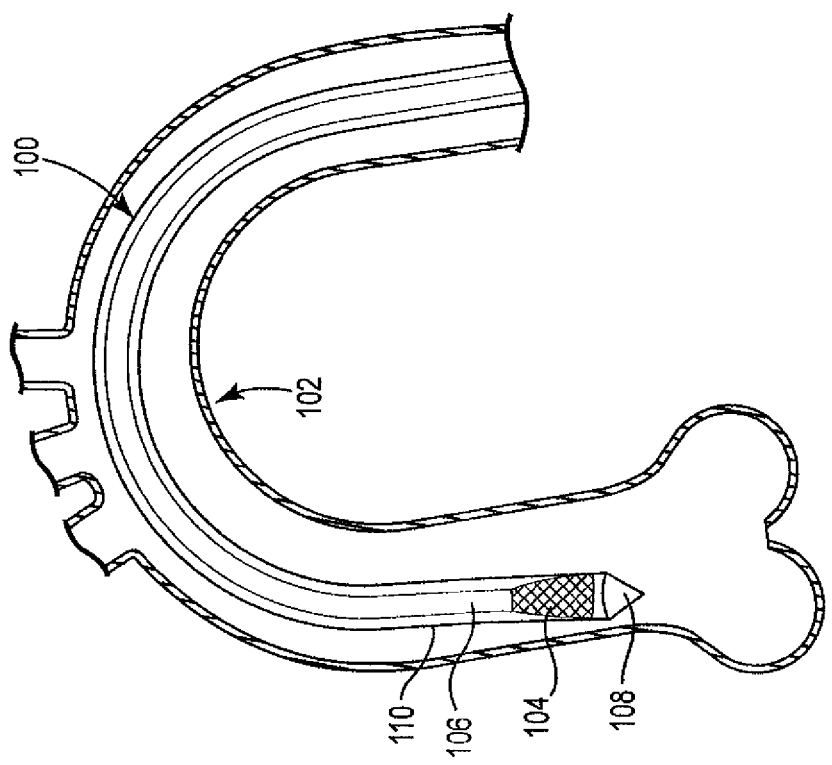
FIG. 7 is a front view of another embodiment of an emboli guarding device on a delivery system within a heart structure, with a mesh structure in a collapsed condition.

Another aspect of the emboli guarding features of the invention is illustrated in FIGS. 7 and 8. In particular, a guide catheter 100 is illustrated as being positioned within an aortic arch 102 of a patient. FIG. 7 shows the guide catheter 100 with a self-expanding mesh portion 104 adjacent to its distal end in a compressed or collapsed condition. In this Figure, guide catheter 100 can be driven over a guidewire (not shown) to position the device in a desired location above the aortic valve in the ascending aorta. FIG. 8 illustrates the mesh portion 104 in an expanded condition. In order to expand the mesh portion 104 in this way, an outer sheath 110 is pulled proximally to expose and therefore expand the mesh portion 104. A tip 108, which can be collapsible, of the delivery system 100 can be pulled proximally out of the guide catheter 100. This will provide an access channel through which another device can be inserted. For example, a delivery system can be advanced through the guide catheter 100 to a position adjacent to the aortic valve.

The mesh portion 104 can expand to the size and shape of the vessel in which it is positioned. In this way, the mesh portion 104 can provide embolic protection during delivery of a device (e.g., a transcatheter valve) and/or during balloon valvuloplasty procedures. That is, the mesh portion 104 is made of a material or materials that allow blood flow, yet that filter out emboli, particles, and/or air bubbles that are undesirably large during other processes. Further, the mesh portion 104 may comprise wires and/or film materials that provide a desired level of particle filtering. It is further noted that the expansion of the mesh portion 104 provides a centering function for the delivery system 100 within the ascending aorta. In this way, better coaxial alignment can occur between a transcatheter valve that is being delivered via the delivery system and the annulus during positioning and release thereof, for example. In this embodiment, once any other processes are completed, such as transcatheter valve delivery and deployment or balloon valvuloplasty, the outer sheath 110 can be advanced in a distal direction to collapse the mesh portion 104 for removal of the device from the body.

The distal end of the guide catheter can also function to align and/or direct a delivery system that is advanced within the guide catheter to an anatomical target, such as the aortic valve, for example. Providing these capabilities of being able to more accurately align and direct the delivery system can help to optimize the accuracy and reliability with which an implant or therapy can be introduced.

With either of the mesh portions described above relative to FIGS. 5 and 6 or FIGS. 7 and 8, the mesh portions preferably are sufficiently sized so that they can expand to match the size and shape of the vessel in which they are located. The mesh portions are also preferably made of a material that provides sufficient force against the walls of the vessel to prevent emboli from moving between the mesh portion and the vessel. Further, the mesh portions can additionally include one or more sections or areas, having a thin film or material that may or may not include fenestrations, such as is described above relative to FIGS. 1-3, for example.

The present invention has now been described with reference to several embodiments thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A device for directing particle flow in a bloodstream, the device comprising:

a frame extending between an inflow end and an outflow end having a semi-circular cross-section, the frame having a vessel anchoring portion and an internal fluid passageway extending between the inflow and outflow ends; and a filtering sheet affixed to the frame and extending across a diameter of the outflow end of the frame.

2. The device of claim 1, wherein the frame includes at least one linear portion and at least one curved portion, such that a plane of the at least one linear portion extends through an interior area of the vessel anchoring portion.

3. The device of claim 1, wherein the filtering sheet comprises a thin film material comprising multiple fenestrations extending through its thickness.

4. The device of claim 3, wherein the size of the fenestrations are selected to prevent particles in the bloodstream that are larger than the fenestrations from moving through the filtering sheet from the internal fluid passageway of the frame.

5. The device of claim 1, wherein the filtering sheet comprises a sheet of pericardial material.

6. The device of claim 1, wherein the frame is configured to match the shape of a portion of an aortic arch of a patient.

7. The device of claim 1, wherein the frame is compressible and expandable.

8. The device of claim 7, wherein the frame comprises a self-expanding material.

9. The device of claim 7, wherein the frame comprises a material that is expandable with the application of an outward radial force.

10. The device of claim 1, wherein the internal fluid passageway has an outer periphery that is defined by the frame and the filtering sheet, wherein the frame extends around a first portion of the outer periphery of the fluid passageway and the filtering sheet extends around a second portion of the outer periphery of the fluid passageway.

11. The device of claim 10, wherein the filtering sheet extends along only a portion of the length of the frame.

12. A method of percutaneously delivering a device to an aortic arch of a patient, the method comprising the steps of:

providing a device comprising a frame extending between an inflow end and an outflow end having a semi-circular cross-section, the frame having a vessel anchoring portion and an internal fluid passageway extending between the inflow and outflow ends, and a filtering sheet affixed to the frame and extending across a diameter of the outflow end of the frame;

compressing the device;

loading the device on a delivery system;

percutaneously delivering the device to the aortic arch with the delivery system; and expanding the device within the aortic arch.

13. The method of claim 12, wherein the filtering sheet comprises a thin film material with multiple fenestrations extending through its thickness, wherein the size of the fenestrations are selected to prevent particles in the bloodstream that are larger than a predetermined size from moving through the filtering sheet from the internal fluid passageway.

14. The method of claim 12, wherein the step of delivering the device comprises positioning the device within the aortic arch so that the filtering sheet is positioned adjacent to the brachiocephalic trunk, the left common carotid artery, and the left subclavian artery.

15. The method of claim 12, wherein the step of expanding the device within the aortic arch comprises the step of removing an external compressive force from the frame.

16. The method of claim 12, wherein the step of expanding the device within the aortic arch comprises the step of applying a radial outward force to the frame.

* * * * *